(12) United States Patent
Lim et al.

(10) Patent No.: US 6,437,029 B1
(45) Date of Patent: Aug. 20, 2002

(54) FLAME RETARDANT POLYCARBONATE RESIN COMPOSITION

(75) Inventors: Jong-Cheol Lim, Kyongki-do; Kyung-Hoon Seo, Seoul; Sam-Joo Yang, Kyungki-do, all of (KR)

(73) Assignee: Cheil Industries Inc., Kyungbuk (KR)

( * ) Notice: Subject to any disclaimer, the term of this patent is extended or adjusted under 35 U.S.C. 154(b) by 38 days.

(21) Appl. No.: 09/752,814

(22) Filed: Dec. 29, 2000

(30) Foreign Application Priority Data

Oct. 31, 2000 (KR) ........................................ 2000-64325

(51) Int. Cl.7 .......................... C08L 69/00; C08K 5/523; C08K 5/5373
(52) U.S. Cl. ........................... 524/97; 524/96; 524/127; 524/141; 525/67; 525/133; 525/148
(58) Field of Search .......................... 525/67, 133, 148; 524/96, 97, 127, 141

(56) References Cited

U.S. PATENT DOCUMENTS

| | | | |
|---|---|---|---|
| 3,462,515 A | 8/1969 | Cantrill | |
| 4,248,976 A | 2/1981 | Clubley et al. | 525/2 |
| 4,692,488 A | 9/1987 | Kress et al. | 524/139 |
| 4,883,835 A | 11/1989 | Buysch | 524/504 |
| 4,983,658 A | 1/1991 | Kress et al. | 524/141 |
| 5,030,675 A | 7/1991 | Wittmann et al. | 524/130 |
| 5,061,745 A | 10/1991 | Wittmann et al. | 524/139 |
| 5,194,495 A | 3/1993 | Lundy et al. | |
| 5,204,394 A | 4/1993 | Gosens et al. | 524/125 |
| 5,244,971 A | 9/1993 | Jean-Marc | |
| 5,292,786 A | 3/1994 | Gaggar et al. | |
| 5,426,159 A | 6/1995 | Umemura | |
| 5,672,645 A | 9/1997 | Eckel et al. | 524/127 |
| 5,723,526 A | 3/1998 | Nagasawa | |
| 5,910,538 A | 6/1999 | Padwa et al. | |
| 6,140,399 A | 10/2000 | Munro | |
| 6,262,173 B1 * | 7/2001 | Kurata | |

FOREIGN PATENT DOCUMENTS

JP 59-202240 11/1984

OTHER PUBLICATIONS

Pending Claims of copending Ser. No. 09 612 114 filed Jul. 7, 2000.

* cited by examiner

Primary Examiner—David J. Buttner
(74) Attorney, Agent, or Firm—Maria Parrish Tungol

(57) ABSTRACT

The present invention relates to a flame retardant thermoplastic resin composition that comprises a polycarbonate resin, a rubber modified styrene-grafted copolymer, a styrene-containing copolymer, a (meth)acrylic acid ester copolymer, a phosphoric acid ester as a flame retardant and a fluorinated polyolefin resin, which does not show coalescence of the domain resin that might be caused by the low viscosity at a high temperature, and poor flame retardancy, weld-line strength and mechanical properties such as impact strength, and which has a good balance of physical properties such as impact strength, heat resistance, heat stability, processability and appearance.

22 Claims, No Drawings

FLAME RETARDANT POLYCARBONATE RESIN COMPOSITION

FIELD OF THE INVENTION

The present invention relates to a flame retardant thermoplastic resin composition. More particularly, the present invention relates to a flame retardant thermoplastic resin composition that comprises a polycarbonate resin, a rubber modified styrene-grafted copolymer, a styrene-containing copolymer, a (meth)acrylic acid ester copolymer, a phosphoric acid ester as a flame retardant and a fluorinated polyolefin resin.

BACKGROUND OF THE INVENTION

Polycarbonate resin is excellent in transparency, mechanical strength and heat resistance, therefore, the resin is widely applied to electric or electronic goods, automobile parts, office supplies, etc. However, the polycaronate resin has poor processability and notched impact strength. In order to overcome the shortcomings, the polycarbonate resin is blended with other polymer resin(s). For example, a blend of a polycarbonate resin and a rubber modified styrene grafted polymer is a resin composition which has improved processability maintaining the good notched impact strength.

The polycarbonate resin compositions should further have good flame retardancy as well as high mechanical strength because the resin compositions are applied to electric or electronic goods, automobile parts, office supplies, etc. When such blends of polycarbonate resin and styrene-containing copolymer are retained at a high temperature during extrusion or injection, the domain size is getting larger. If the viscosity of the blend becomes lower, the domain size is easily getting larger. If the domain size is getting larger, the mechanical properties of a molded article are rapidly deteriorated.

To provide the polycarbonate resin with good flame retardancy, a halogen-containing flame retardant and/or an antimony-containing compound were used. U.S. Pat. Nos. 4,983,658 and 4,883,835 disclose resin compositions employing a halogen-containing compound as flame retardant. However, the disadvantages could be observed that the halogen-containing compound results in the corrosion of the mold itself by the hydrogen halide gases released during the molding process and is fatally harmful due to the toxic gases liberated in case of fire. Especially, since a polybromodiphenyl ether, mainly used for a halogen-containing flame retardant, can produce toxic gases such as dioxin or furan during combustion, flame retardants which are prepared without a halogen-containing compound have become a major concern in this field.

A general method is employ a phosphoric acid ester compound as flame retardant to provide the polycarbonate resin with flame retardancy without using a halogen-containing compound. However, the more phosphoric acid ester compound is used, the lower the heat resistance of the resin composition is getting and the more easily the coalescence of the domain resin occurs. The is large sized domain resin functions as a fuel source when combusting, resulting that the combustion time is lengthened not to give good flame retardancy. Further the resin composition containing a low molecular phosphoric acid ester has a poor weld-line strength.

U.S. Pat. No. 5,292,786 discloses a resin composition composed of a polycarbonate resin, an ABS resin, a phosphorous flame retardant and a polyalkylmethacrylate resin. However, if the polyalkylmethacrylate resin is used in excess of a certain amount, the polyalkylmethacrylate resin is depolymerized and results in poor heat resistance, appearance and flame retardancy.

The present inventors have developed a flame retardant thermoplastic resin composition that comprises a polycarbonate resin, a rubber modified styrene-grafted copolymer, a styrene-containing copolymer, a (meth)acrylic acid ester copolymer, a phosphoric acid ester as a flame retardant and a fluorinated polyolefin resin, which does not show coalescence of the domain resin that might be caused by the low viscosity at a high temperature, lowering of flame retardancy, weld-line strength and mechanical properties such as impact strength, and which has a good balance of physical properties such as impact strength, heat resistance, heat stability, processability and appearance.

OBJECTS OF THE INVENTION

A feature of the present invention is the provision of a flame retardant thermoplastic resin composition that does not show coalescence of the domain resin that might be caused by the low viscosity at a high temperature during extrusion or injection.

Another feature of the present invention is the provision of a flame retardant thermoplastic resin composition with good flame retardancy.

A further feature of the present invention is the provision of a flame retardant thermoplastic resin composition with good mechanical properties such as impact strength at a high temperature during extrusion or injection.

A further feature of the present invention is the provision of a flame retardant thermoplastic resin composition with good weld-line strength.

A further feature of the present invention is the provision of a flame retardant thermoplastic resin composition with a good balance of physical properties such as impact strength, heat resistance, heat stability, processability and appearance.

Other objects and advantages of this invention will be apparent from the ensuing disclosure and appended claims.

SUMMARY OF THE INVENTION

A flame retardant thermoplastic resin composition according to the present invention comprises (A) about 45 to 95 parts by weight of a polycarbonate resin, (B) about 1 to 50 parts by weight of a rubber modified styrene-grafted copolymer prepared by graft-polymerizing ($b_1$) about 5 to 95 parts by weight of a monomer mixture consisting of about 50 to 95% by weight of styrene, α-methylstyrene, halogen- or alkyl-substituted styrene or a mixture thereof and about 5 to 50% by weight of acrylonitrile, methacrylonitrile, maleic acid anhydride, $C_{1-4}$ alkyl- or phenyl N-substituted maleimide or a mixture thereof onto ($b_2$) about 5 to 95 parts by weight of a rubber polymer selected from the group consisting of butadiene rubber, acryl rubber, ethylene-propylene rubber, styrene-butadiene rubber, acrylonitrile-butadiene rubber, isoprene rubber, copolymer of ethylene-propylene-diene (EPDM), polyorganosiloxane-polyalkyl(meth) acrylate rubber or a mixture thereof, (C) about 0.5 to 50 parts by weight of a styrene-containing copolymer polymerized with ($c_1$) about 50 to 95% by weight of styrene, α-methylstyrene, halogen- or alkyl-substituted styrene or a mixture thereof and ($c_2$) about 5 to 50% by weight of acrylonitrile, methacrylonitrile, maleic acid anhydride, $C_{1-4}$ alkyl- or phenyl N-substituted maleimide or a mixture thereof, (D) about 0.5 to 50 parts by weight of a (meth) acrylic acid ester copolymer polymerized with ($d_1$) about 44 to 90% by weight of a $C_{1-8}$ methacrylic acid alkyl ester, a $C_{1-8}$ acrylic acid alkyl ester, or a mixture thereof, ($d_2$) about 5 to 55% by weight of styrene, α-methylstyrene, halogen- or alkyl-substituted styrene or a mixture thereof and ($d_3$) about 1 to 20% by weight of acrylonitrile, methacrylonitrile, or a mixture thereof, (E) about 1 to 30 parts by weight of a phosphoric acid ester as a flame retardant, and (F) about 0.05 to 5.0 parts by weight of a fluorinated polyolefin resin with average particle size of about 0.05 to 1000 μm and density of about 1.2 to 2.3 g/cm³ as per 100 parts by weight of (A)+(B)+(C)+(D).

DETAILED DESCRIPTION OF THE INVENTION

A flame retardant thermoplastic resin composition according to the present invention comprises (A) about 45 to 95 parts by weight of a polycarbonate resin, (B) about 1 to 50 parts by weight of a rubber modified styrene-grafted copolymer, (C) about 0.5 to 50 parts by weight of a styrene-containing copolymer, (D) about 0.5 to 50 parts by weight of a (meth)acrylic acid ester copolymer, (E) about 1 to 30 parts by weight of a phosphoric acid ester as a flame retardant, and (F) about 0.05 to 5.0 parts by eight of a fluorinated polyolefin resin. Each component will be described in detail as follow:

(A) Polycarbonate Resin

The polycarbonate resin is prepared by reacting a diphenol represented by the following formula (I) with a phosgene, a halogen formiate or a carboxylic acid diester:

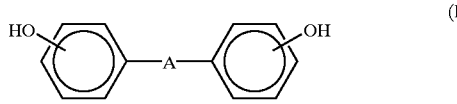

(I)

where A is a single bond, a $C_{1-5}$ alkylene group, a $C_{2-5}$ alkylidene group, a $C_{5-6}$ cycloalkylidene group, S or $SO_2$.

The examples of the diphenol include hydroquinone, resorcinol, 4,4'-dihydroxydiphenol, 2,2-bis-(4-hydroxyphenyl)-propane, 2,4-bis-(4-hydroxyphenyl)-2-methylbutane, 1,1-bis-(4-hydroxyphenyl)-cyclohexane, 2,2-bis-(3-chloro-4-hydroxyphenyl)-propane, and 2,2-bis-(3,5-dichloro-4-hydroxyphenyl)-propane. More preferable diphenols are 2,2-bis-(4-hydroxyphenyl)-propane, 2,2-bis-(3,5-dichloro-4-hydroxyphenyl)-propane, and 1,1-bis-(4-hydroxyphenyl)-cyclohexane, and the most preferable diphenol is 2,2-bis-(4-hydroxyphenyl)-propane called 'bisphenol A'.

In the present invention it is preferable that the polycarbonate resin (A) has a weight average molecular weight ($M_w$) of about 10,000 to 200,000, more preferably about 15,000 to 80,000.

A polycarbonate with branched chains may be preferably used. In particular a compound with 3 valences or above may be added in an amount of about 0.05 to 2 mol % per the total moles of the diphenol to be used. A homopolymer of polycarbonate, a copolymer of polycarbonate or a mixture thereof may be used in this invention. Some portion of the polycarbonate resin may be replaced with an aromatic polyester-carbonate resin that is obtained by polymerization in the presence of an ester precursor, such as difunctional carboxylic acid. The polycarbonate resin is used in an amount of about 45 to 95 parts by weight as per the flame retardant thermoplastic resin composition according to the present invention.

(B) Rubber Modified Styrene-Grafted Copolymer

The rubber modified styrene-grafted copolymer according to the resent invention is prepared by graft-polymerizing ($b_1$) about 5 to 95 parts by weight of a monomer mixture consisting of about 50 to 95% by weight of styrene, α-methylstyrene, halogen- or alkyl-substituted styrene or a mixture thereof and about 5 to 50% by weight of acrylonitrile, methacrylonitrile, maleic acid anhydride, $C_{1-4}$ alkyl- or phenyl N-substituted maleimide or a mixture thereof onto ($b_2$) about 5 to 95 parts by weight of a rubber polymer selected from the group consisting of butadiene rubber, acryl rubber, ethylene-propylene rubber, styrene-butadiene rubber, acrylonitrile-butadiene rubber, isoprene rubber, copolymer of ethylene-propylene-diene (EPDM), polyorganosiloxane-polyalkyl(meth)acrylate rubber or a mixture thereof.

Preferable examples of the rubber modified styrene-grafted copolymer are grafted-polymers obtained by graft polymerizing a mixture of styrene and acrylonitrile is grafted onto butadiene rubber, acryl rubber or styrene-butadiene rubber. The most preferable example of the rubber modified styrene-grafted copolymer is a grafted-polymer that a mixture of styrene and acrylonitrile is grafted onto butadiene rubber, which is called acrylonitrile-butadiene-styrene (ABS) resin.

The rubber modified styrene-grafted copolymer is used in an amount of about 1 to 50 parts by weight as per the flame retardant thermoplastic resin composition according to the present invention. The rubber polymer to prepare the rubber modified styrene-grafted copolymer has preferably an average particle size of about 0.05 to 4.0 μm considering the impact strength and appearance.

The rubber modified styrene-grafted copolymer according to the present invention can be prepared by a conventional polymerization process. However, the copolymer can be preferably prepared by the emulsion or bulk process in which vinyl monomers are added to the rubber polymer using an initiator.

(C) Styrene-Containing Copolymer

The styrene-containing copolymer is a copolymer that is polymerized with ($c_1$) about 50 to 95% by weight of styrene, α-methylstyrene, halogen- or alkyl-substituted styrene or a mixture thereof and ($c_2$) about 5 to 50% by weight of acrylonitrile, methacrylonitrile, maleic acid anhydride, $C_{1-4}$ alkyl- or phenyl N-substituted maleimide or a mixture thereof A mixture of the copolymers may be used as the component (C). The styrene-containing copolymer is used in an amount of about 0.5 to 50 parts by weight as per the flame retardant thermoplastic resin composition according to the present invention.

The styrene-containing copolymer can be produced as by-products when preparing the rubber modified styrene-grafted copolymer (B). The by-products are mostly produced when an excess of monomers are grafted onto a small amount of rubber polymer or when a chain transferring agent is used in excess. The amount of the styrene-containing copolymer to be used in this invention does not include the amount of the by-products that might be produced during preparation of the rubber modified styrene-grafted copolymer (B). The styrene-containing copolymer is a thermoplastic resin that does not contain a rubber polymer component.

The preferable examples of the styrene-containing copolymer are a copolymer of styrene and acrylonitrile, a copolymer of α-methylstyrene and acrylonitrile, and a copolymer of styrene, α-methylstyrene and acrylonitrile. The styrene-containing copolymer is preferably prepared by emulsion, suspension, solution or bulk process, and has a weight average molecular weight ($M_w$) of about 15,000 to 200,000.

Another preferable example of the styrene-containing copolymer is a copolymer of styrene and maleic acid anhydride, which is prepared by a continuous bulk process or a solution process. The maleic acid anhydride is preferably used in the amount of about 5 to 25% by weight. The copolymer of styrene and maleic acid anhydride has a weight average molecular weight ($M_w$) of about 60,000 to 200,000 and an intrinsic viscosity of about 0.3 to 0.9.

The styrene for preparation of the component (C) in this invention can be replaced by p-methylstyrene, vinyltoluene, 2,4-dimethylstyrene or α-methylstyrene.

(D) (Meth)acrylic Acid Ester Copolymer

The (meth)acrylic acid ester copolymer is prepared by polymerizing ($d_1$) about 44 to 90% by weight of a $C_{1-8}$ methacrylic acid alkyl ester, a $C_{1-8}$ acrylic acid alkyl ester, or a mixture thereof, ($d_2$) about 5 to 55% by weight of styrene, α-methylstyrene, halogen- or alkyl-substituted styrene or a mixture thereof and ($d_3$) about 1 to 20% by weight of acrylonitrile, methacrylonitrile, or a mixture thereof.

The $C_{1-8}$ methacrylic acid alkyl ester is obtained from methacrylic acid and monohydryl alcohol containing 1 to 8 carbon atoms and $C_{1-8}$ acrylic acid alkyl ester from acrylic acid and monohydryl alcohol containing 1 to 8 carbon atoms. The examples of the acid alkyl ester include methacrylic acid methyl ester, methacrylic acid ethyl ester, acrylic acid methyl ester, acrylic acid ethyl ester, and methacrylic acid propyl ester. Methacrylic acid methyl ester is the most preferable.

The (meth)acrylic acid ester copolymer according to the present invention functions as a compatibilizing agent. The (meth)acrylic acid ester Copolymer shows good compatibility with the components (A), (B) and (C), resulting to improve the compatibility of the flame retardant resin composition.

The (meth)acrylic acid ester copolymer is preferably prepared by emulsion, suspension, solution or bulk process, and has a weight average molecular weight ($M_w$) of about 20,000 to 300,000.

The (meth)acrylic acid ester copolymer is used in an amount of about 0.5 to 50 parts by weight as per the flame retardant thermoplastic resin composition according to the present invention, preferably about 1 to 40 parts by weight.

(E) Phosphoric Acid Ester as Flame Retardant

The phosphoric acid ester as a flame retardant in this invention is classified into three flame retardants as follow, which can be used separately or in combination as a mixture.

(E$_1$) Phosphoric Acid Ester

The phosphoric acid ester is represented by the following formula (II), which is disclosed in Japanese Patent Publication No. 59-202,240. The phosphoric acid ester may be used in single or in combination as a mixture.

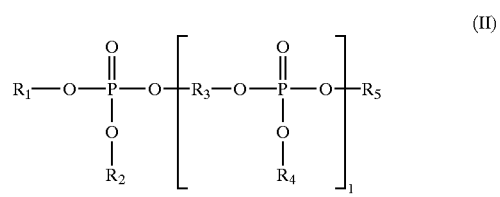

where $R_1$, $R_2$, $R_4$ and $R_5$ are a $C_{6-20}$ aryl group or an alkyl-substituted $C_{6-20}$ aryl group, respectively, preferably a phenyl group or an alkyl-substituted phenyl group in which alkyl is methyl, ethyl, isopropyl, t-butyl, isobutyl, isoamyl or t-amyl, preferably methyl, ethyl, isopropyl or t-butyl;

$R_3$ is a $C_{6-30}$ aryl group or an alkyl-substituted $C_{6-30}$ aryl group, preferably resorcinol, hydroquinone or bisphenol-A; and l means number average degree of polymerization and is a value of 0 to 3.

In the present invention, it is preferable to use an oligomer type phosphoric acid ester that is a derived from a $C_{6-30}$ aryl group and has an average value of l of about 0 to 3. The oligomer type phosphoric acid ester is a mixture of oligomers in which l is 0, 1, 2 and 3, respectively.

The representative examples of the phosphoric acid ester with l=0 are tri(alkylphenyl)phosphate, di(alkylphenyl) monophenylphosphate, diphenylmono(alkylphenyl) phosphate and triphenylphosphate. The phosphoric acid ester can be used in single or in combination as a mixture.

(E$_2$) Phosphoric Acid Ester Morpholide Compound

The phosphoric acid ester morpholide compound is represented by the following formula (III), which is used in single or in combination as a mixture. The compound is prepared by reacting phosphorous oxychloride (POCl$_3$) with aromatic alcohol and morpholine.

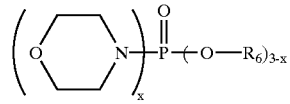

where $R_6$ is a $C_{6-20}$ aryl group or an alkyl-substituted $C_{6-20}$ aryl group, preferably a phenyl group, a cresyl group, a t-butylphenyl group, or an isopropylphenyl group, and x is an integer of 1 to 3. More preferably, $R_6$ is a phenyl group or a cresyl group, and x is 1 or 2.

The methods of preparation of the phosphoric acid ester morpholide compound are not limited, but the compound is generally prepared by reacting phosphorous oxychloride (POCl$_3$) with aromatic alcohol and morpholine. The phosphoric acid ester morpholide compound may contain triarylphosphate up to 20% by weight during preparation. The compound containing triarylphosphate may be used without or after purification. In case using of a mixture of the phosphoric acid ester morpholide compounds, the phosphoric acid ester morpholide compound of x=1 is about 1 to 99% by weight, the phosphoric acid ester morpholide compound of x=2 is about 1 to 99% by weight, and the phosphoric acid ester morpholide compound of x=3 is about 0 to 20% by weight.

(E$_3$) Oligomer Type Phosphoric Acid Ester Morpholide Compound

The oligomer type phosphoric acid ester morpholide compound is represented by the following formula (IV), which is used in single or in combination as a mixture. The compound is prepared by reacting an aryl compound such as resorcinol, hydroquinone and bisphenol-A with arylmorpholinochlorophosphate in a conventional process.

(IV)

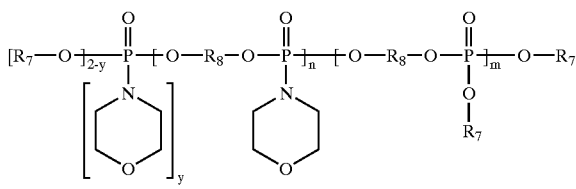

where $R_7$ is a $C_{6-20}$ aryl group or an alkyl-substituted $C_{6-20}$ aryl group, $R_8$ is a $C_{6-30}$ aryl group or an alkyl-substituted $C_{6-30}$ aryl group, y is 1 or 2, and m and n mean number average degree of polymerization and m+n is 0 to 3.

Preferably $R_7$ is a phenyl group or an alkyl-substituted phenyl group in which alkyl is methyl, ethyl, isopropyl, t-butyl, isobutyl, isoamyl or t-amyl, preferably methyl, ethyl, isopropyl or t-butyl, and $R_8$ is resorcinol, hydroquinone or bisphenol-A.

In the present invention, it is preferable to use an oligomer type phosphoric acid ester morpholide compound having an average value of n+m of about 0 to 3. The oligomer type phosphoric acid ester morpholide compound can be used as a mixture of oligomers in which n+m is 0, 1, 2 and 3, respectively.

The methods of preparation of the oligomer type phosphoric acid ester morpholide compound are not limited, but the compound is generally prepared by reacting an aryl compound such as resorcinol, hydroquinone and bisphenol-A with arylmorpholinochlorophosphate in the presence of a catalyst by a conventional process. The arylmorpholinochlorophosphate is prepared by reacting phosphorous oxychloride ($POCl_3$) with aromatic alcohol and morpholine. Diarylchlorophosphate and dimorpholinochlorophosphate can be synthesized up to 20% by weight in the preparation process of the arylmorpholinochlorophosphate. The oligomer type phosphoric acid ester morpholide compound synthesized in accordance with the method above may contain about 0 to 10% by weight of a phosphoric acid ester morpholide compound of m+n=0, about 50 to 100% by weight of a phosphoric acid ester morpholide compound of m+n=1, about 0 to 40% by weight of a phosphoric acid ester morpholide compound of m+n=2 or over. The oligomer type phosphoric acid ester morpholide compound may be used without or after purification.

(F) Fluorinated Polyolefin Resin

The fluorinated polyolefin resin (F) according to the present invention is prepared by a conventional process, for example, the resin is prepared in an aqueous solvent at 7~71 kg/cm2 and 0~200° C., preferably 20~100° C., in the presence of a free radical forming catalyst such as sodium-, potassium-, or ammonium-peroxydisulphate.

The examples of the fluorinated polyolefin resin are polytetrafluoroethylene, polyvinylidenefluoride, tetrafluoroethylene/vinylidenefluoride copolymer, tetrafluoroethylene/hexafluoropropylene copolymer, and ethylene/tetrafluoroethylene copolymer. The fluorinated polyolefin resin may be used in single or in combination as a mixture. The fluorinated polyolefin resin has preferably average particle size of about 0.05 to 1000 μm and density of about 1.2 to 2.3 g/cm³. The fluorinated polyolefin resin functions to form a fibrillar network when the resin composition containing the fluorinated polyolefin resin is extruded, resulting to increase the flow viscosity and to increase the shrinkage during combustion so as to prevent the dripping phenomena. The fluorinated polyolefin resin is used in emulsion state or in powder state. In case using in emulsion state, dispersion of the fluorinated polyolefin resin is good, but the process will be somewhat complicated. Accordingly, if the fluorinated polyolefin resin could be uniformly dispersed in the entire resin composition to form the fibrillar network structure, it is preferable to use the fluorinated polyolefin resin in powder state.

The fluorinated polyolefin resin is used in an amount of about 0.5 to 5.0 parts by weight as per 100 parts by weight of (A)+(B)+(C)+(D) of the flame retardant thermoplastic resin composition according to the present invention.

Other additives may be contained in the resin composition of the present invention. The additives include an additional flame retardant, a lubricant, a releasing agent, an anti-dripping agent, an impact modifier, a plasticizer, a heat stabilizer, an oxidation inhibitor, a light stabilizer, a compatibilizer and the like. An inorganic filler such as talc, silica, mica, glass fiber, an organic or inorganic pigment and/or dye can be added too. The additives are employed in an amount of about 0 to 60 parts by weight as per 100 parts by weight of (A)+(B)+(C) of the flame retardant thermoplastic resin composition, preferably about 1 to 40 parts by weight.

The flame retardant thermoplastic resin composition according to the present invention can be prepared by a conventional method. All the components and additives are mixed together and extruded through an extruder and are prepared in the form of pellets.

The flame retardant thermoplastic resin composition according to the present invention can be applied to electric or electronic goods, automobile parts, office supplies, etc which require good flame retardancy, weld-line strength and impact strength.

The invention may be better understood by reference to the following examples which are intended for the purpose of illustration and are not to be construed as in any way limiting the scope of the present invention, which is defined in the claims appended hereto. In the following examples, all parts and percentage are by weight unless otherwise indicated.

EXAMPLES

The components to prepare flameproof thermoplastic resin compositions in Examples 1~5 and Comparative Examples 1~4 are as follows:

(A) Polycarbonate Resin

Bisphenol-A type polycarbonate resin with a weight average molecular weight ($M_w$) of about 25,000 was used as the polycarbonate resin (B) Rubber Modified Styrene-Grafted Copolymer 45 parts of butadiene rubber latex powder, 36 parts of styrene, 14 parts of acrylonitrile and 150 parts of deionized water were mixed. To the mixture, 1.0 parts of potassium oleate, 0.4 parts of cumenhydroperoxide, and 0.3 parts of mercaptan-containing chain transfer agent were added. The blend was kept at 75° C. for 5 hours to obtain ABS latex. To the ABS latex, 1% sulfuric acid was added, coagulated and dried to obtain styrene-containing graft copolymer resin (g-ABS) in powder form.

(C) Styrene-Containing Copolymer 71 parts of styrene, 29 parts of acrylonitrile, 120 parts of deionized water and 0.2 parts of azobisisobutylonitrile were blended. To the blend, 0.5 parts of tricalciumphosphate and 0.3 parts of mercaptan-containing chain transfer agent were added. The resultant solution was heated to 80° C. for 90 minutes and kept for 180 minutes. The resultant was washed, dehydrated and dried. Styrene-acrylonitrile copolymer (SAN) was obtained.

(D) (Meth)acrylic Acid Ester Copolymer 70 parts of methacrylic acid ester, 20 parts of styrene, 10 parts of acrylonitrile, 120 parts of deionized water and 0.2 parts of azobisisobutylonitrile were blended. To the blend, 0.5 parts of tricalciumphosphate and 0.3 parts of mercaptan-containing chain transfer agent were added. The resultant solution was heated to 80° C. for 90 minutes and kept for 180 minutes. The resultant was washed, dehydrated and dried.

(E) Phosphoric Acid Ester as Flame Retardant ($E_{1a}$) The bisphenol-A type phosphoric acid ester represented by the chemical formula (II) is used, where $R_1$, $R_2$, $R_4$ and $R_5$ are a phenyl group, which consists of 3.4% by weight of the compound of l=0, 85.4% by weight of the compound of l=1, and 11.1% by weight of the compound of l=2, and which has an average of l=1.0.

($E_{1b}$) Triphenylphosphate of l=0 in the chemical formula (II) was used.

($E_2$) The phosphoric acid ester morpholide compound was prepared by reacting phosphorous oxychloride ($POCl_3$) with morpholine, which is represented by the chemical formula (III) is used, where $R_6$ is a phenyl group, which consists of 86% by weight of the compound of x=1, and 5% by weight of the compound of x=2.

($E_3$) The oligomer type phosphoric acid ester morpholide compound was prepared by reacting resorcinol with arylmorpholinochlorophosphate, which is represented by the chemical formula (IV) is used, where $R_7$ is a phenyl group and $R_8$ is a resorcinol derivative, which consists of 1.5% by weight of the compound of m+n=0 and y=1, 68.4% by weight of the compound of m+n=1 and y=1, and 30.1% by weight of the compound of m+n>2 and y=1.

(F) Fluorinated Polyolefin Resin

Teflon (registered trademark) 7 AJ by Dupont company was used.

EXAMPLES 1–5

The components as shown in Table 1, an antioxidant and a heat stabilizer were mixed in a conventional mixer and the mixture was extruded through a twin screw extruder with L/D=35 and ∅=45 mm at 240° C. to prepare in pellet form. The resin pellets were molded into test specimens.

Comparative Examples 1–4

The Comparative Examples 1–4 were conducted in the same manner as in Examples 1–4, respectively, except that polymethylmethacrylate resin(D') (product by LG Chemical Co. of Korea) was used. The components of the comparative examples are shown in Table 1.

TABLE 1

|  | Examples | | | | | Comparative Examples | | | |
| --- | --- | --- | --- | --- | --- | --- | --- | --- | --- |
|  | 1 | 2 | 3 | 4 | 5 | 1 | 2 | 3 | 4 |
| (A) | 73 | 80 | 80 | 70 | 70 | 73 | 80 | 80 | 70 |
| (B) | 10 | 10 | 10 | 10 | 10 | 10 | 10 | 10 | 10 |
| (C) | 7 | 5 | 5 | 7 | 10 | 7 | 10 | — | 20 |
| (D) | 10 | 5 | 5 | 13 | 10 | — | — | — | — |
| (D') | — | — | — | — | — | 10 | — | 10 | — |
| (E) |  |  |  |  |  |  |  |  |  |
| ($E_{1a}$) | 10 | — | — | 10 | — | 10 | — | — | — |
| ($E_{1b}$) | 2 | — | — | — | — | 2 | — | 12 | — |
| ($E_2$) | — | 12 | 2 | 2 | — | — | 12 | — | — |
| ($E_3$) | — | — | 10 | — | 12 | — | — | — | 12 |
| (F) | 0.4 | 0.4 | 0.4 | 0.4 | 0.4 | 0.4 | 0.4 | 0.4 | 0.4 |

Measurement of Physical Properties:

(1) Heat Stability

The test specimens of Examples 1–5 and Comparative Examples 1–4 were heated at 20° C./min at the atmosphere of nitrogen and the temperatures to start degradation of the specimens were observed by measuring the loss of mass of the specimens. The temperatures of degradation of the resin composition were observed after volatilization of the flame retardant used.

(2) Weld-Line Strength and Physical Properties

The specimens for measuring weld-line strength and physical properties were prepared by a 10 oz extruder at 250° C. The specimens were kept at the relative humidity of 50% for 40 hours. The physical properties were measured in accordance with ASTM D256.

(3) Physical Properties at High Extrusion Temperature

The specimens for measuring physical properties were prepared by a 10 oz extruder at 280° C. The specimens were kept at the relative humidity of 50% for 40 hours. The physical properties were measured in accordance with ASTM D256.

(4) Flame Retardancy

The specimens for measuring flame retardancy were prepared by a 10 oz extruder at 250° C. The specimens were kept at the relative humidity of 50% for 40 hours. The flame retardancy were measured in accordance with UL94VB. For each Example and Comparative Example, five specimens were tested for combustion time and average combustion time.

(5) Heat Resistance

The heat resistance was measured in accordance with ASTM D1525.

The test results of Examples 1–5 and Comparative Examples 1–4 are shown in Table 2. Methacrylic acid ester copolymer was used as a compatibilizing agent in Examples 1–5, polymethylmethacrylate was used as a compatibilizing agent in Comparative Examples 1 and 3, and no compatibilizing agent was used in Comparative Examples 2 and 4.

TABLE 2

| | Examples | | | | | Comparative Examples | | | |
|---|---|---|---|---|---|---|---|---|---|
| | 1 | 2 | 3 | 4 | 5 | 1 | 2 | 3 | 4 |
| UL94VB (1/12") | V-0 | V-0 | V-0 | V-0 | V-0 | V-1 | V-0 | V-2 | V-2 |
| Average Combustion | | | | | | | | | |
| Time (sec) | 2.0 | 2.2 | 2.1 | 1.9 | 2.7 | 3.2 | 3.5 | 4.6 | 8.5 |
| Max. Combustion | | | | | | | | | |
| Time (sec) | 4 | 5 | 5 | 4 | 6 | 11 | 9 | 12 | 15 |
| Drippings/Tests | 0/5 | 0/5 | 0/5 | 0/5 | 0/5 | 0/5 | 0/5 | 2/5 | 2/5 |
| High Temperature | | | | | | | | | |
| Impact Strength (1/8") | | | | | | | | | |
| (kg.cm/cm) | 33 | 35 | 33 | 30 | 31 | 28 | 12 | 27 | 11 |
| Weld-Line | | | | | | | | | |
| Impact Strength (1/8") | | | | | | | | | |
| (kg.cm/cm) | 14 | 15 | 15 | 13 | 13 | 13 | 10 | 13 | 9 |
| VST (° C.) | 91 | 90 | 94 | 90 | 90 | 91 | 91 | 90 | 91 |
| Degradation Temp. (° C.) | 405 | 411 | 412 | 401 | 406 | 383 | 416 | 385 | 415 |

As shown in Table 2, the resin compositions employing compatibilizing agent has flame retardancy of V–0 regardless of the amount of polycarbonate resin. However, in case not using compatibilizing agent, the flame retardancy of V–0 can be obtained only if polycarbonate resin is used in a large amount. However, in this case, combustion time is variable, and the time can be longer sometimes. The resin compositions employing compatibilizing agent are superior to the resin compositions not employing compatibilizing agent in weld-line impact strength, high temperature notched impact strength and heat stability.

On the other hand, in case of Comparative Examples 1 and 3 using polymethylmethacrylate as a compatibilizing agent, the resin compositions show good weld-line strength and high temperature notched impact strength, but poor heat stability. In addition, in this case, combustion time is variable, and the time can be longer sometimes.

The present invention can be easily carried out by an ordinary skilled person in the art. Many modifications and changes may be deemed to be with the scope of the present invention as defined in the following claims.

What is claimed is:

1. A flame retardant thermoplastic resin composition comprising:

(A) about 45 to 95 parts by weight of a polycarbonate resin;

(B) about 1 to 50 parts by weight of a rubber modified styrene-grafted copolymer prepared by graft-polymerizing ($b_1$) about 5 to 95 parts by weight of a monomer mixture comprising about 50 to 95% by weight of styrene, α-methylstyrene, halogen- or alkyl-substituted styrene or a mixture thereof and about 5 to 50% by weight of acrylonitrile, methacrylonitrile, maleic acid anhydride, $C_{1-4}$ alkyl- or phenyl N-substituted maleimide or a mixture thereof onto ($b_2$) about 5 to 95 parts by weight of a rubber polymer selected from the group consisting of butadiene rubber, acryl rubber, ethylene-propylene rubber, styrene-butadiene rubber, acrylonitrile-butadiene rubber, isoprene rubber, copolymer of ethylene-propylene-diene (EPDM), polyorganosiloxane-polyalkyl(meth)acrylate rubber or a mixture thereof;

(C) about 0.5 to 50 parts by weight of a styrene-containing copolymer polymerized with ($c_1$) about 50 to 95% by weight of styrene, α-methylstyrene, halogen- or alkyl-substituted styrene or a mixture thereof and ($c_2$) about 5 to 50% by weight of acrylonitrile, methacrylonitrile, maleic acid anhydride, $C_{1-4}$ alkyl- or phenyl N-substituted maleimide or a mixture thereof;

(D) about 0.5 to 50 parts by weight of a (meth)acrylic acid ester copolymer polymerized with ($d_1$) about 44 to 90% by weight of a methacrylic acid alkyl ester, a $C_{1-8}$ acrylic acid alkyl ester, or a mixture thereof, ($d_2$) about 5 to 55% by weight of styrene, α-methylstyrene, halogen- or alkyl-substituted styrene or a mixture thereof and ($d_3$) about 1 to 20% by weight of acrylonitrile, methacrylonitrile, or a mixture thereof;

(E) about 1 to 30 parts by weight of a phosphoric acid ester as a flame retardant; and (F) about 0.05 to 5.0 parts by weight of a fluorinated polyolefin resin with average particle size of about 0.05 to 1000 μm and density of about 1.2 to 2.3 g/cm³ as per 100 parts by weight of (A)+(B)+(C)+(D), wherein said phosphoric acid ester is a compound ($E_1$) has the following formula (II):

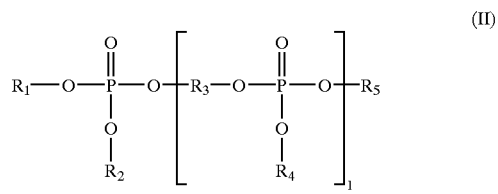

where $R_1$, $R_2$, $R_4$ and $R_5$ are a $C_{6-20}$ aryl group or an alkyl-substituted $C_{6-20}$ aryl group, respectively and $R_3$ is $C_{6-30}$ aryl group or an alkyl-substituted $C_{6-30}$ aryl group; and 1 means number average degree of polymerization and is a value of 0 to 3.

2. The flame retardant thermoplastic resin composition as defined in claim 1, wherein said $C_{1-8}$ methacrylic acid alkyl ester is selected from the group consisting of methacrylic acid methyl ester, methacrylic acid ethyl ester and methacrylic acid propyl ester and said $C_{1-8}$ acrylic, acid alkyl ester is selected from the group consisting of acrylic acid methyl ester and acrylic acid ethyl ester.

3. The flame retardant thermoplastic resin composition as defined in claim 1, wherein said $R_1$, $R_2$, $R_4$ and $R_5$ are a phenyl group or an alkyl-substituted phenyl group in which alkyl is methyl, ethyl, isopropyl or t-butyl.

4. The flame retardant thermoplastic resin composition as defined in claim 1, wherein said $R_3$ is a resorcinol, hydroquinone or bisphenol-A group.

5. A molded article produced from the flame retardant thermoplastic resin composition as defined in claim 1.

6. A flame retardant thermoplastic resin composition comprising:
(A) about 70 to 80 parts by weight of a polycarbonate resin;
(B) about 10 parts by weight of a rubber modified styrene-grafted copolymer prepared by graft-polymerizing
($b_1$) about 5 to 95 parts by weight of a monomer mixture comprising about 36 parts by weight of styrene and about 14 parts by weight of acrylonitrile,
($b_2$) about 45 parts by weight of a butadiene rubber;
(C) about 5 to 10 parts by weight of a styrene-containing copolymer polymerized with
($c_1$) about 75 parts by weight of styrene, and
($c_2$) about 29 parts by weight of acrylonitrile;
(D) about 5 to 13 parts by weight of a (meth)acrylic acid ester copolymer polymerized with
($d_1$) about 70 parts by weight methacrylic acid ester,
($d_2$) about 20 parts by weight of styrene, and
($d_3$) about 10 parts by weight of acrylonitrile;
(E) about 2 to 12 parts by weight of a phosphoric acid ester as a flame retardant; and
(F) about 0.4 parts by weight of a fluorinated polyolefin resin with average particle size of about 0.05 to 1000 μm and density of about 1.2 to 2.3 g/cm³ as per 100 parts by weight of (A)+(B)+(C)+(D),
wherein said phosphoric acid ester is triphenyl phosphate, or a compound ($E_1$) represented by the formula (II) or mixtures thereof:

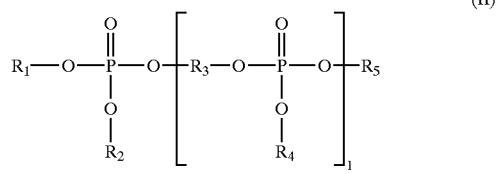

(II)

where $R_1$, $R_2$, $R_4$ and $R_5$ are phenyl groups, $R_3$ is a resorcinol, hydroquinone or bisphenol-A group, and l is 1.0

7. The flame retardant thermoplastic resin composition as defined in claim 6, wherein said phosphoric acid ester (E) is a mixture of compounds ($E_1$) represented by the following formula (II):

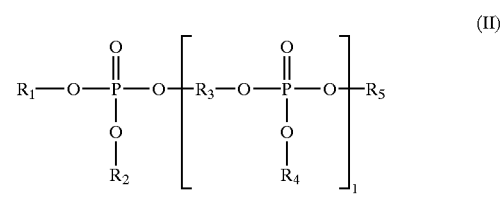

(II)

where $R_1$, $R_2$, $R_4$ and $R_5$ are phenyl groups, $R_3$ is a bisphenol-A group, and 3.4% by weight of the phosphoric acid esters that comprise ($E_1$) have l=0, 85.4% by weight of the phosphoric acid esters that comprise ($E_1$) have l=1, and 11.1% by weight of the phosphoric acid esters that comprise ($E_1$) have l=2.

8. The flame retardant thermoplastic resin composition as defined in claim 6, said phosphoric acid ester (E) is triphenylphosphate.

9. A flame retardant thermoplastic resin composition comprising:
(A) about 45 to 95 parts by weight of a polycarbonate resin;
(B) about 1 to 50 parts by weight of a rubber modified styrene-grafted copolymer prepared by graft-polymerizing
($b_1$) about 5 to 95 parts by weight of a monomer mixture comprising about 50 to 95% by weight of styrene, α-methylstyrene, halogen- or alkyl-substituted styrene or a mixture thereof and about 5 to 50% by weight of acrylonitrile, methacrylonitrile, maleic acid anhydride, $C_{1-4}$ alkyl- or phenyl N-substituted maleimide or a mixture thereof onto ($b_2$) about 5 to 95 parts by weight of a rubber polymer selected from the group consisting of butadiene rubber, acryl rubber, ethylene-propylene rubber, styrene-butadiene rubber, acrylonitrile-butadiene rubber, isoprene rubber, copolymer of ethylene-propylene-diene (EPDM), polyorganosiloxane-polyalkyl(meth)acrylate rubber or a mixture thereof;
(C) about 0.5 to 50 parts by weight of a styrene-containing copolymer polymerized with
($c_1$) about 50 to 95% by weight of styrene, α-methylstyrene, halogen- or alkyl-substituted styrene or a mixture thereof and
($c_2$) about 5 to 50% by weight of acrylonitrile, methacrylonitrile, maleic acid anhydride, $C_{1-4}$ alkyl- or phenyl N-substituted maleimide or a mixture thereof;
(D) about 0.5 to 50 parts by weight of a (meth)acrylic acid ester copolymer polymerized with
($d_1$) about 44 to 90% by weight of a methacrylic acid alkyl ester, a $C_{1-8}$ acrylic acid alkyl ester, or a mixture thereof,
($d_2$) about 5 to 55% by weight of styrene, α-methylstyrene, halogen- or alkyl-substituted styrene or a mixture thereof and
($d_3$) about 1 to 20% by weight of acrylonitrile, methacrylonitrile, or a mixture thereof;
(E) about 1 to 30 parts by weight of a phosphoric acid ester as a flame retardant; and
(F) about 0.05 to 5.0 parts by weight of a fluorinated polyolefin resin with average particle size of about 0.05 to 1000 μm and density of about 1.2 to 2.3 g/cm₃ as per 100 parts by weight of (A)+(B)+(C)+(D),
wherein said phosphoric acid ester is a compound ($E_2$) having the following formula (III),

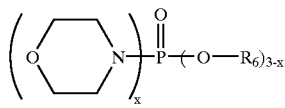

(III)

where $R_6$ is a $C_{6-20}$ aryl group or an alkyl-substituted $C_{6-20}$ aryl group, and x is an integer of 1 to 3.

10. The flame retardant thermoplastic resin composition as defined in claim 9, wherein said $C_{1-8}$ methacrylic acid alkyl ester is selected from the group consisting of methacrylic acid methyl ester, methacrylic acid ethyl ester and methacrylic acid ester and said $C_{1-8}$ acrylic acid alkyl ester is selected from the group consisting of acrylic acid methyl ester and crylic acid ethyl ester.

11. The flame retardant thermoplastic resin composition as defined in claim 9, wherein said $R_6$ is a phenyl group, a cresyl group, a t-butylphenyl group, or an isopropylphenyl group.

12. The flame retardant thermoplastic resin composition as defined in claim 9, wherein said x is 1 or 2.

13. A molded produced from the flame retardant thermoplastic resin composition as defined in claim 9.

14. A flame retardant thermoplastic resin composition comprising:

(A) about 70 to 80 parts by weight of a polycarbonate resin;

(B) about 10 parts by weight of a rubber modified styrene-grafted copolymer prepared by graft-polymerizing
  ($b_1$) about 5 to 95 parts by weight of a monomer mixture comprising about 36 parts by weight of styrene and about 14 parts by weight of acrylonitrile,
  ($b_2$) about 45 parts by weight of a butadiene rubber;

(C) about 5 to 10 parts by weight of a styrene-containing copolymer polymerized with
  ($c_1$) about 75 parts by weight of styrene, and
  ($c_2$) about 29 parts by weight of acrylonitrile;

(D) about 5 to 13 parts by weight of a (meth)acrylic acid ester copolymer polymerized with
  ($d_1$) about 70 parts by weight methacrylic acid ester,
  ($d_2$) about 20 parts by weight of styrene, and
  ($d_3$) about 10 parts by weight of acrylonitrile;

(E) about 2 to 12 parts by weight of a phosphoric acid ester as a flame retardant; and (F) about 0.4 parts by weight of a fluorinated polyolefin resin with average particle size of about 0.05 to 1000 μm and density of about 1.2 to 2.3 g/cm³ as per 100 parts by weight of (A)+(B)+(C)+(D), wherein said phosphoric acid ester is a compound ($E_2$) represented by the following formula (III), or mixtures thereof:

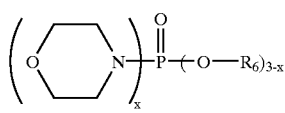

(III)

where R6 is a phenyl group and x is an integer of 1 in 86% by weight of the phosphoric acid esters that comprise ($E_2$) and x is an integer of 2 in 5% by weight of the phosphoric acid esters that comprise ($E_2$).

15. The flame retardant thermoplastic resin composition as defined in claim 14, wherein said phosphoric acid ester (E) is a mixture of compounds ($E_2$) represented by the following formula (III):

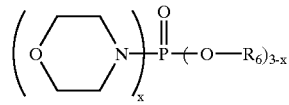

(III)

where $R_6$ is a phenyl group and x is an integer of 1 in 86% by weight of the phosphoric acid esters that comprise ($E_2$) and x is an integer of 2 in 5% by weight of the phosphoric acid esters that comprise ($E_2$).

16. A flame retardant thermoplastic resin composition produced by adding and mixing together the following separate components:

(A) about 45 to 95 parts by weight of a polycarbonate resin;

(B) about 1 to 50 parts by weight of a rubber modified styrene-grafted copolymer prepared by graft-polymerizing
  ($b_1$) about 5 to 95 parts by weight of a monomer mixture comprising about 50 to 95% by weight of styrene, α-methylstyrene, halogen- or alkyl-substituted styrene or a mixture thereof and about 5 to 50% by weight of acrylonitrile, methacrylonitrile, maleic acid anhydride, $C_{1-4}$ alkyl- or phenyl N-substituted maleimide or a mixture thereof onto
  ($b_2$) about 5 to 95 parts by weight of a rubber polymer selected from the group consisting of butadiene rubber, acryl rubber, ethylene-propylene rubber, styrene-butadiene rubber, acrylonitrile-butadiene rubber, isoprene rubber, copolymer of ethylene-propylene-diene (EPDM), polyorganosiloxane-polyalkyl(meth)acrylate rubber or a mixture thereof;

(C) about 0.5 to 50 parts by weight of a styrene-containing copolymer polymerized with
  ($c_1$) about 50 to 95% by weight of styrene, α-methylstyrene, halogen- or alkyl-substituted styrene or a mixture thereof and
  ($c_2$) about 5 to 50% by weight of acrylonitrile, methacrylonitrile, maleic acid anhydride, $C_{1-14}$ alkyl- or phenyl N-substituted maleimide or a mixture thereof;

(D) about 0.5 to 50 parts by weight of a (meth)acrylic acid ester copolymer polymerized with
  ($d_1$) about 44 to 90% by weight of a methacrylic acid alkyl ester, a $C_{1-8}$ acrylic acid alkyl ester, or a mixture thereof,
  ($d_2$) about 5 to 55% by weight of styrene, α-methylstyrene, halogen- or alkyl-substituted styrene or a mixture thereof and
  ($d_3$) about 1 to 20% by weight of acrylonitrile, methacrylonitrile, or a mixture thereof;

(E) about 1 to 30 parts by weight of a phosphoric acid ester as a flame retardant; and (F) about 0.05 to 5.0 parts by weight of a fluorinated polyolefin resin with average particle size of about 0.05 to 1000 μm and density of about 1.2 to 2.3 g/cm³ as per 100 parts by weight of (A)+(B)+(C)+(D), wherein said phosphoric acid ester is a compound ($E_1$) has the following formula (II):

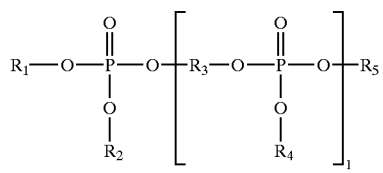

(II)

where $R_1$, $R_2$, $R_4$ and $R_5$ are a $C_{6-20}$ aryl group or an alkyl-substituted $C_{6-20}$ aryl group, respectively and $R_3$ is $C_{6-30}$ aryl group or an alkyl-substituted $C_{6-30}$ aryl group; and l means number average degree of polymerization and is a value of 0 to 3.

17. The flame retardant thermoplastic resin composition as defined in claim 16, wherein said $R_1$, $R_2$, $R_4$ and $R_5$ are a phenyl group or an alkyl-substituted phenyl group in which alkyl is methyl, ethyl, isopropyl or t-butyl.

18. The flame retardant thermoplastic resin composition as defined in claim 16, wherein said $R_3$ is a resorcinol, hydroquinone or bisphenol-A group.

19. The flame retardant thermoplastic resin composition as defined in claim 16, where $R_1$, $R_2$, $R_4$ and $R_5$ are phenyl groups, $R_3$ is a resorcinol, hydroquinone or bisphenol-A group, and l is 1.0.

20. A flame retardant thermoplastic resin composition produced by adding and mixing together the following separate components:

(A) about 45 to 95 parts by weight of a polycarbonate resin;

(B) about 1 to 50 parts by weight of a rubber modified styrene-grafted copolymer prepared by graft-polymerizing
  ($b_1$) about 5 to 95 parts by weight of a monomer mixture comprising about 50 to 95% by weight of styrene, α-methylstyrene, halogen- or alkyl-substituted styrene or a mixture thereof and about 5 to 50% by weight of acrylonitrile, methacrylonitrile, maleic acid anhydride, $C_{1-4}$ alkyl- or phenyl N-substituted maleimide or a mixture thereof onto
  ($b_2$) about 5 to 95 parts by weight of a rubber polymer selected from the group consisting of butadiene rubber, acryl rubber, ethylene-propylene rubber, styrene-butadiene rubber, acrylonitrile-butadiene rubber, isoprene rubber, copolymer of ethylene-propylene-diene (EPDM), polyorganosiloxane-polyalkyl(meth)acrylate rubber or a mixture thereof;

(C) about 0.5 to 50 parts by weight of a styrene-containing copolymer polymerized with
  ($c_1$) about 50 to 95% by weight of styrene, a:-methylstyrene, halogen- or alkyl-substituted styrene or a mixture thereof and
  ($c_2$) about 5 to 50% by weight of acrylonitrile, methacrylonitrile, maleic acid anhydride, $C_{1-14}$ alkyl-or phenyl N-substituted maleimide or a mixture thereof;

(D) about 0.5 to 50 parts by weight of a (meth)acrylic acid ester copolymer polymerized with
  ($d_1$) about 44 to 90% by weight of a methacrylic acid alkyl ester, a $C_{1-8}$ acrylic acid alkyl ester, or a mixture thereof,
  ($d_2$) about 5 to 55% by weight of styrene, (α-methylstyrene, halogen- or alkyl-substituted styrene or a mixture thereof and
  ($d_3$) about 1 to 20% by weight of acrylonitrile, methacrylonitrile, or a mixture thereof;

(E) about 1 to 30 parts by weight of a phosphoric acid ester as a flame retardant; and (F) about 0.05 to 5.0 parts by weight of a fluorinated polyolefin resin with average particle size of about 0.05 to 1000 μm and density of about 1.2 to 2.3 g/cm₃ as per 100 parts by weight of (A)+(B)+(C)+(D), wherein said phosphoric acid ester is a compound ($E_2$) having the following formula (III) or mixtures thereof:

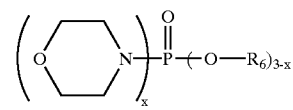

(III)

where $R_6$ is a $C_{6-20}$ aryl group or an alkyl-substituted $C_{6-20}$ aryl group, and x is an integer of 1 to 3.

21. The flame retardant thermoplastic resin composition as defined in claim 20, wherein said $R_6$ is a phenyl group, a cresyl group, a t-butylphenyl group, or an isopropylphenyl group.

22. The flame retardant thermoplastic resin composition as defined in claim 20, wherein said phosphoric acid ester (E) is a mixture of compounds ($E_2$) represented by the following formula (III):

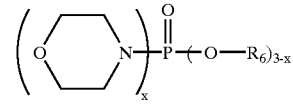

(III)

where $R_6$ is a phenyl group and x is an integer of 1 in 86% by weight of the phosphoric acid esters that comprise ($E_2$) and x is an integer of 2 in 5% by weight of the phosphoric acid esters that comprise ($E_2$).

* * * * *